United States Patent [19]

Poznansky

[11] Patent Number: 4,749,570
[45] Date of Patent: Jun. 7, 1988

[54] TARGETING CONJUGATES OF ALBUMIN AND THERAPEUTIC AGENTS

[75] Inventor: Mark J. Poznansky, Alberta, Canada

[73] Assignee: The Governors of the University of Alberta, Edmonton, Canada

[21] Appl. No.: 815,752

[22] Filed: Dec. 31, 1985

Related U.S. Application Data

[63] Continuation of Ser. No. 336,412, Dec. 31, 1981, abandoned.

[51] Int. Cl.$^4$ .................. A61K 37/48; A61K 39/375
[52] U.S. Cl. ..................................... 424/94.3; 424/85
[58] Field of Search .............. 424/85, 94, 94.1, 94.3, 424/94.6; 435/177, 201, 229, 188, 189

[56] References Cited

U.S. PATENT DOCUMENTS

| | | | |
|---|---|---|---|
| 4,046,722 | 9/1977 | Rowland | 424/85 |
| 4,110,432 | 8/1978 | Wilkinson et al. | 424/88 |
| 4,161,519 | 7/1979 | Talwar | 424/88 |
| 4,241,177 | 12/1980 | Singh et al. | 260/112 R |

OTHER PUBLICATIONS

Remy, et al., The Lancet, Jul. 8, 1978, pp. 68–70.
Achord et al., Cell, vol. 15, pp. 269–278, 1978.
Tager, H., et al., Nature, vol. 281, pp. 122–125, 1979.
Basu, S., et al., Proc. Natl. Acad. Sci, vol. 73, pp. 3178–3182, 1976.
Cunningham, A., Understanding Immunology, Academic Press, New York, pp. 19–21, 1978.
Shier, W., et al., Int. J. Cancer, vol. 18, pp. 672–678, 1976.
Hurwitz, E., et al., Cancer Research, vol. 35, pp. 1175–1181, 1975.
Witztum, J., et al., Proc. Natl. Acad. Sci., vol. 80, pp. 2757–2761. 1983.

*Primary Examiner*—Blondel Hazel
*Attorney, Agent, or Firm*—Banner, Birch, McKie and Beckett

[57] ABSTRACT

The invention provides a conjugate comprising an enzyme having its antigenic sites or antigenicity masked by albumin and having a tageting agent attached, and a method for its preparation. The album is included in an amount sufficient to mask antigenicity of the enzyme. The targeting agent used has binding specificity for receptor sites on cells towards which it is desirable to direct the enzyme. Insulin, immunoglobulin G, antibody against human pancreatic tumor cell, and antibody against hyaluronic acid are exemplified as targeting agents.

11 Claims, No Drawings

TARGETING CONJUGATES OF ALBUMIN AND THERAPEUTIC AGENTS

This application is a continuation of application Ser. No. 336,412 filed Dec. 31, 1981 now abandoned.

BACKGROUND OF THE INVENTION

The present invention relates to conjugates of therapeutic agents, namely enzymes, for the treatment of certain diseases in mammals.

The term therapeutic agent includes a large number of enzymes which are used in the treatment of genetic, metabolic diseases. These diseases include a wide range of inborn errors of metabolism in which specific enzymes in the body are either deficient or defective. Suitable enzyme replacement might provide an appropriate therapy. In other diseases, cancer for example, certain cells have been shown to be sensitive to a specific enzyme. For example, in acute lymphocytic leukemia the tumor cells are sensitive to the enzyme L-asparaginase. The tumor cells have an absolute requirement for exogenous L-asparagine and cannot survive in the presence of L-asparaginase, the enzyme responsible for the removal of the substrate. Enzyme treatment of this type is usually termed enzyme therapy.

There are problems associated with the injection of many of the enzymes into the body. Firstly, the enzyme may be foreign to the body and can therefore cause the body's immune system to mount a rejection reaction. The enzyme is then rapidly cleared from the body following each subsequent administration. This rejection reaction, in its severest form called an anaphylactic reaction, may threaten the life of the recipient.

Secondly, the enzyme is frequently heat labile and sensitive to proteolysis by other circulating enzymes. Rapid bioinactivation of the enzyme can occur. This may necessitate repeated administration of large dose of said enzyme. In addition to the expense and bother which this causes, there is also the increased risk of complicating the above described immunological reaction, thereby increasing the possibility of anaphylaxis.

Thirdly, it is often necessary or desirable to deliver or target said enzyme to specific body cells or organs requiring action. For instance, in many enzyme deficiency diseases the defect is intracellular. Due to the lack of a functioning enzyme, the substrate which accumulates in the body cell is compartementalized in intracellular organelles termed lysosomes. Frequently, the substrate is stored only in specific tissues or organs. Thus to effect enzyme replacement it may be necessary to target the enzymes to these specific sites. This has proven to be a major limitation to the treatment of such fatal childhood enzyme deficiency diseases as lipid storage diseases and glycogen storage diseases.

Some, but not all, of the above problems have been solved in the prior art by conjugating the therapeutic agent with a carrier. Carriers are divided into two groups, those that cause highly specific binding to cell-surface receptors and those that do not. The former type of carrier will hereinafter be referred to as a targeting agent.

Targeting of drugs is well documented, see for example the review article by M. J. Poznansky and L. G. Cleland in *Drug Delivery Systems*, ed. Juliano, Oxford University Press, New York, 1980, pg. 253-315. Targeting agents are molecules, frequently biological macromolecules, which bind to specific receptor sites on the surfaces of body cells. Known targeting agents include serum hormones, antibodies against cell surface antigens, and lectins.

It is also known in the prior art to protect therapeutic agents by conjugating with an appropriate carrier. Conjugates of albumin and therapeutic agents are documented in the above-referenced review article and in an article by M. J. Poznansky and D. Bhardwaj in Canadian Journal of Physiology and Pharmacology, 58, 1980, pg. 322-325. These albumin conjugatesd have been shown to be both non-immunogenic and non-antigenic, see for instance M. H. Remy and M. J. Poznansky, The Lancet, July 8, 1978, pg. 68-70. The albumin is believed to mask the antigenic sites on the therapeutic agent such that the recipient recognizes the conjugate as self and therefore does not mount an immune response. Further, these albumin conjugates have been shown to be more resistant to bioinactivation than was the free therapeutic agent.

To my knowledge, no attempt has been made to target these albumin-protected therapeutic agents. Prior to the present invention it was not known whether a targeting agent would be effective in targeting such a large and complex molecule. Further, it was not known whether attachment of a targeting agent would interfere with the biological activity of the albumin-therapeutic agent conjugate.

SUMMARY OF THE INVENTION

I have discovered that conjugates of albumin and enzyme can be made targetable by chemically linking the conjugate to a targeting agent having binding specificity for receptor sites on body cells against which it is desirable to direct the enzyme. Known targeting agents, including serum hormones, cell-surface directed antibodies, and lectins, are suitable for this purpose.

While it might have been expected that the albumin molecules would mask or interfere with the targetability of the targeting agent, once it was linked to the enzyme-albumin conjugate, this was found not to be the case. The targeting agent, linked to the conjugate, was found to retain its ability to specifically deliver the conjugate to specific cellular surface receptors. Further, the targeting agent was found not to interfere with the ability of the body cell to utilize the therapeutic agent once the conjugate was delivered to the cell. This was not a predictable property of the conjugates of the present invention.

The albumin is included in the conjugate in an amount sufficient to mask the antigenicity of the therapeutic agent. The term 'to mask the antigenicity' is meant to infer that the conjugate does not illicit an immune response. The albumin used is most preferably homologous to the mammal intended as the recipient. Since in most cases the intended recipient is human, human serum albumin is preferred. Other sources of albumin, for example bovine serum albumin and horse serum albumin are useful for therapy in cattle and horses respectively.

As explained, the targeting agent allows for delivery of the conjugates to specific cellular surface receptors. The choice of targeting agent therefore depends on the desired site of delivery. The present invention exemplifies the use of insulin, immunoglobulin G, antibody against human pancreatic tumor cells, and antibody against hepatocytes as targeting agents. Insulin is an example of a serum hormone while the rest are examples of cell-surface directed antibodies.

The therapeutic agent in the conjugates is chosen from the known enzymes used in the treatment of disease in mammals. The conjugates of the present invention are illustrated with three examples, namely α-1,4-glucosidase, superoxide dismutase, and L-asparaginase. Each of these enzymes is chemically linked to carrier albumin and one of the above-listed targeting agents to demonstrate the targetability and effectiveness of the conjugates.

A deficiency of the α-1,4-glycosidase enzyme in humans is known as Pompe's disease or Type II glycogen-storage disease. The deficiency causes death, usually be cardio-respiratory failure, before the age of 2 years. The absence of this enzyme results in the intra-cellular accumulation of glycogen in what are believed to be lysosomes in the liver and in both respiratory and cardiac muscle. The conjugates of the present invention with α-1,4-glucosidase are shown to retain the enzyme activity after cross-linking to the albumin carrier and the targeting agent. The conjugates are also shown to be non-immunogenic. Further, the conjugates are shown to greatly enhance the amount of the α-1,4-glucosidase enzyme delivered to muscle cells.

As mentioned previously, L-asparaginase has the potential of being an important therapeutic agent against acute lymphocytic leukemia. Conjugates of L-asparaginase, albumin and targeting agent are shown to be non-immunogenic, biologically active and targetable to specific cell types, for example human pancreatic tumor cells.

Superoxide dismutase (SOD) may be used as a therapeutic agent in the treatment of rheumatoid arthritis where it may act to reduce superoxide free radicals. The conjugate of SOD, albumin and antibodies against hyaluronic acid may be targeted to joint tissue known to be susceptible to this form of arthritis.

The process used to chemically link the therapeutic agent to the carrier albumin and in turn to the targeting agent depends on the functional groups of the particular enzyme and targeting agent. The linking process should be chosen to preserve water solubility of the final conjugate product, to preserve the activity of the enzyme, and also to preserve the site specific binding capability of the targeting agent. In most cases the linking process utilizes a cross-linking agent between the enzyme and the carrier albumin and between the carrier albumin and the targeting agent. Glutaraldehyde, sodium periodate and water soluble carbodiimide are exemplified as suitable cross-linking agents in the specific conjugates illustrated herein.

Broadly stated the invention provides a novel composition of matter, comprising, in water soluble, sterile and non-immunogenic form, an enzyme chemically linked to homologous albumin and a targeting agent chemically linked to the albumin, the amount of albumin being sufficient to mask the antigenicity of the enzyme, and the targeting agent having binding specificity for receptor sites on cells to which it is desirable to direct the enzyme.

The present invention also provides a process for producing a water soluble, sterile and non-immunogenic conjugate of an enzyme with homologous albumin and a targeting agent, comprising the steps of: (a) cross-linking the enzyme with an amount of albumin sufficient to mask the antigenicity of the therapeutic agent; (b) cross-linking the resulting complex of the enzyme and the albumin with a targeting agent having binding specificity for recptor sites on cells against which it is desirable to direct the enzyme, said binding specificity being retained after the cross-linking reaction.

DESCRIPTION OF THE PREFERRED EMBODIMENT

The three component conjugates of the present invention are useful in delivering enzymes to specific body cells, tissues or organs in mammals for the treatment of disease.

The enzymes which can be delivered in this form are usually those for which the characteristics of avoiding immunological reactivity by antigenicity masking and site specific targeting are desired. The enzymes useful in the conjugates include those enzymes causitive of enzyme deficiency diseases and those enzymes intended for enzyme therapy. A partial list of enzyme deficiency diseases together with the enzyme responsible for the deficiency is included in Table I. Exemplary enzymes for enzyme therapy purposes include L-asparaginase, uricase and superoxide dismutase. Persons skilled in the art will know of other therapeutic agents which would be desirably conjugated in accordance with the present invention.

TABLE I

| DOCUMENTED ENZYME DEFICIENCY DISEASES | |
| --- | --- |
| Disease | Enzyme |
| Acatalasia | Catalase |
| Albinism | Tyrosinase |
| Alcaptonuria | Homogentisic Acid Oxidase |
| Cholesteryl Ester Deficiency | Lecithin Cholesterol Acyltransferase |
| Cystathioninuria | Cystathionase |
| Disaccharide Intolerance III | Lactase |
| Fructose Intolerance | Fructose-1-Phosphate Aldolase |
| Fructosuria | Hepatic Fructokinase |
| Galactosemia | Galactose-1-Phosphate Uridyl Transferase |
| Gangliosidosis (GMl) | β-Galactosidase A, B, C, |
| Gaucher's Disease | Glucocerebrosidase |
| G6PD Deficiency | Glucose-6-Phosphate Dehydrogenase |
| Glycogen Storage Disease I | Glucose-6-Phosphatase |
| Glycogen Storage Disease II | α-1,4-Glucosidase |
| Glycogen Storage Disease III | Amylo-1,6-Glucosidase |
| Glycogen Storage Disease V | Muscle Phosphorylase |
| Glycogen Storage Disease VI | Liver Phosphorylase |
| Glycogen Storage Disease VII | Muscle Phosphofructokinase |
| Glycogen Storage Disease VIII | Liver Phosphorylase Kinase |
| Hemolytic Anemia | Glucose-6-Phosphate Dehydrogenase |
| Hemolytic Anemia | Phosphoglycerate Kinase |
| Hemolytic Anemia | Pyruvate Kinase |
| Histidinemia | Histidase |
| Homocytinuria I | Cystathionine Synthetase |
| Hydroxyprolinemia | Hydroxyproline Oxidase |
| Hyperlipoproteinemia II | Lipoprotein Lipase |
| Hyperlysinemia | Lysine-Ketoglutarate Reductase |
| Hypoglycemia (Acidosis) | Fructose-1,6-Diphosphatase |
| Immunodeficiency Disease | Adenosine Deaminase |
| Intestinal Lactase Deficiency | Lactase |
| Krabbe's Disease | A β-Galactosidase |
| Lesch-Nyhan Syndrome | Hypoxanthine-Guanine Phosphoribosyl Transferase |
| Mannosidosis | α-Mannosidase |
| Maple Sugar Urine Disease | Keto Acid Decarboxylase |
| Metachromatic Leukodystrophy | Arylsulfatase A |
| Mucopolysaccharidosis I | α-L-Iduronidase |
| Mucopolysaccharidosis III | Heparin Sulphate Sulphatase |
| Mucopolysaccharidosis VI | Arylsulfatase B |
| Mucopolysaccharidosis VII | β-Glucoronidase |
| Niemann-Pick Disease | Sphingomyelinase |
| Orotic Aciduria II | Orotidylic Decarboxylase |
| Pentosuria | L-Xylulose Reductase |
| Phenylketonuria | Phenylalanine Decarboxylase |

TABLE I-continued

DOCUMENTED ENZYME DEFICIENCY DISEASES

| Disease | Enzyme |
| --- | --- |
| Pyruvate Carboxylase Def. | Pyruvate Carboxylase |
| Richner-Hanhart Syndrome | Tyrosine Aminotransferase |
| Sandhoff's Disease | Hexosaminidase A, B |
| Tay-Sachs Disease | Hexosaminidase A |
| Tyrosinemia | Tyrosine Transaminase |
| Xanthinuria | Xanthine Oxidase |

The albumin carrier is included in the conjugate in a molar excess to the therapeutic agent in order to mask the antigenicity of the therapeutic agent. Homologous albumin is most preferably used in the conjugate so as not to cause the conjugate to trigger an immune response in the recipient mammal. Heterologous albumin may be used only if it does not illicit a pronounced immunological response in the recipient mammal.

The particular targeting agent included in the conjugate is one which has binding specificity for specific receptor sites on cells against which it is desirable to direct the therapeutic agent. The targeting agent is selected from serum hormones, cell-surface directed antibodies and lectins which are known to have receptor sites on specific body cells. Exemplary of suitable targeting agents are insulin, glucagon, epidermal growth factor, low-density lipoprotein, human chorionic gonadrotropin, thyroid stimulating hormone, asialoglycoproteins, mannosyl-terminal glycoproteins, endorphins, enkephalins, transferrin, melanotropin, cell-surface directed antibodies (e.g. antibodies against tumor specific antigens, cell surface antigens, cell surface receptors), human growth hormone, α-2-macroglobulin, melanotropin, plant and human lectins (e.g. peanut lectin, wheat germ lectin, concanavilin A, protein A), and galactose terminal glycoproteins. The amount of targeting agent included in the conjugate has not been found to be critical; however, a molar excess of the targeting agent to the therapeutic agent has been found to improve the delivery of the conjugate to the desired cells.

To prepare the enzyme-albumin-targeting agent conjugates, the enzyme is first chemically linked to the molar excess of albumin. The resulting enzyme-albumin conjugate is thereafter chemically linked to the preferred molar excess of targeting agent. This order of linking is preferably used so that the binding sites of the targeting agent remain substantially clear for binding to receptor sites.

The functionality of the enzyme and targeting agent usually require that a cross-linking agent be used for each of the chemical linking steps. The particular cross-linking agent chosen will of course depend on the functionality of the specific components being linked. The cross-linking agents will usually utilize carboxyl groups, amino groups, sulfhydral groups or sugar residues on one or both of the components to be linked.

A large number of cross-linking agents are known, see for example the previously referenced review article by Poznansky and Cleland (1980). A partial list of suitable cross-linking agents includes glutaraldehyde, water-soluble carbodiimides, sodium periodate (periodate oxidation), dithiothreotol (disulfide reduction), diisocyanate, cyanuric chloride, mixed anhydrides, imidoesters, bisdiazobenzidine, cyanogen bromide, p,p'-difluoro-m,m'-dinitrophenyl sulphone, N-succininidyl-4-iodoacetylaminobenzoate, and diazonium salts.

The conditions for the cross-linking reaction, for example pH, temperature and degree of cross-linking are chosen such that the biological activity of the therapeutic agent, the binding specificity of the targeting agent and the water solubility of the final conjugate are maintained. Each of these characteristics of the final conjugate can be tested for and the cross-linking conditions adjusted accordingly by persons skilled in the art.

The conjugates of the present invention are utilized in a sterile form to treat diseases in warm blooded mammals. To that end the conjugate is injected intramuscularly, subcutaneously, intravenously, intraperitoneally, intracranially or intradermally, depending on the desired site of action, into the recipient patient. Alternatively there may be topical applications of the conjugates. The dosage used will be dependent on such factors as the type and severity of the disease, the size and species of the recipient patient, the toxicity of the therapeutic agent and the degree of targeting attained by the conjugate. The dosage can therefore be worked out by routine experiments with each of the conjugates.

The present invention is exemplified by the following specific embodiments which are meant to be merely illustrative and not limitative of the invention.

EXAMPLE 1

L-Aparaginase-Albumin-Insulin Conjugate Cross-Linked with Glutaraldehyde and Carbodiimide L-Asparaginase (5 mg) obtained from *E. coli* was chemically linked to homologous albumin (25 mg) obtained from mouse or human by reaction with 50 μl of 25% glutaraldehyde in 4 ml of phosphate buffered saline (0.1M potassium phosphate pH 6.8). The reaction was performed at 4° C. for 4 hours in the presence of asparagine (5 mg) in order to protect the active site of the enzyme. The reaction was halted with the addition of glycine (50 mg). The product was then separated from the unreacted monomeric components by dialysis, pressure ultrafiltration or molecular sieve chromatography. The isolated product was then cross-linked to bovine or porcine (15 mg) insulin by reacting the same with water soluble 1-ethyl-3-(3-dimethylaminopropyl) carbodiimide HCl (ECDI—10 mg) at 4° C. for 2 hours. The end product was separated and purified by molecular sieve chromatography which indicated that the final product had a molecular weight ranging from $9 \times 10^5$ to $1.4 \times 10^6$. The calculated mole ratio was 1.5:15:90, L-asparaginase:albumin:insulin.

The resulting L-asparaginase-albumin-insulin conjugate was assayed for enzyme activity in accordance with the technique of Mashburn and Wriston, Arch. Biochem. Biophys., 1964, 105, pg. 450-452. The product (enzyme:albumin:insulin=1:10:60, based on starting quantities) was found to retain about 70% of the starting enzyme activity, as reported in Table II. This represents a significant amount of enzyme activity since, as will be shown below, the enzyme is now in a protected form.

To demonstrate the resistance of the product conjugate to proteolytic inactivation, equal amounts of the enzyme in free and conjugated form were incubated with 5 units of trypsin (Sigma Chemical, St. Louis, Mich.). The enzyme activity monitored as a function of time is reported in Table III. The results show that the enzyme conjugated in accordance with this invention was much more resistant to bioinactivation than was the free enzyme.

To test the binding specificity of the enzyme conjugate, the end product was labelled covalently with $^{125}$Iodine and then incubated with mouse spleen cells. The % binding of the enzyme was determined after 20 minutes at 24° C. in accordance with the procedure of J. R. Gavin, et al., Proc. Natl. Acad. Sci., U.S.A., 71, (1974), 84–90. The results, as reported in Table IV, show that the enzyme conjugate binds to the spleen cells, which are known to possess insulin receptors, to a much greater extent than does the free L-asparaginase or the L-asparaginase-albumin conjugate. The insulin is therefore shown to be an effective targeting agent. Conjugates having insulin to albumin molar ratios ranging from 1:1 to 1:10 (data is given for 1:6) were found to retain the binding qualities of the insulin.

The L-asparaginase-albumin conjugates (absent the targeting agent) were shown to be non-immunogenic in both tissue culture and whole animal experiments in accordance with techniques reported by Remy and Poznansky, the Lancet ii, July 8, 1978, pg. 68–70. The addition of insulin to the conjugates does not affect the immunogenicity of the of the resulting conjugate. The immune response to the free L-asparaginase enzyme is compared to the immune response from the L-asparaginase-albumin conjugates in Table V. The L-asparaginase-albumin conjugates tested had ratios of enzyme to albumin ranging from 1:5 to 1:20. As indicated in the table a molar excess of 10:1 albumin to enzyme is sufficient to mask any antigenicity of the enzyme.

TABLE II

ACTIVITY OF ENZYME AND ENZYME CONJUGATES

| Enzyme Preparation | Enzyme Activity | % Activity Retained |
|---|---|---|
| L-asparaginase | 400 units/mg** | |
| L-asparaginase-albumin | 310 units/mg** | 77.5 |
| L-asparaginase-albumin-IgG | 290 units/mg** | 72.5 |
| L-asparaginase-albumin-(Fab')$_2$ | 301 units/mg** | 69.8 |
| L-asparaginase-albumin-insulin | 280 units/mg** | 70.0 |
| α-1,4-glucosidase | 8.5 units/mg*** | |
| α-1,4-glucosidase-albumin | 6.6 units/mg*** | 77.6 |
| α-1,4-glucosidase-albumin-IgG | 6.0 units/mg*** | 70.5 |
| α-1,4-glucosidase-albumin-insulin | 5.8 units/mg*** | 68.2 |

*% activity retained calculated on a per mg enzyme basis
**E. Coli L-asparaginase assayed as per (Mashburn & Wriston, 1964, Arch. Biochem. Biophys. 105, 450–452.
***1,4-glucosidase assayed as per (de Barsy et al., 1972, Eur. J. Biochem. 31, 156–165) Data is for α-1,4-glucosidase from human placenta.

TABLE III

TRYPSIN SENSITIVITY OF L-ASPARAGINASE-ALBUMIN-INSULIN CONJUGATES

| Enzyme Preparation | T ½ at 37° C.+* 5 Units Trypsin |
|---|---|
| L-asparaginase | 10 min. |
| L-asparaginase-albumin-insulin | 120 min. |

*Equal amounts of enzyme in free and polymeric form were incubated with 5 units of Trypsin (Sigma Chemical, St. Louis MI) and the enzyme activity was monitored as a function of time as per Table II.

EXAMPLE 2

L-Asparaginase-Albumin-Insulin Conjugates Cross-Linked with Glutaraldehyde

Following the procedure of Example 1, L-asparaginase was linked to homologous albumin with the glutaraldehyde cross-linking agent. The resulting enzyme-albumin complex was then cross-linked to insulin using the same glutaraldehyde cross-linking conditions. A molar ratio of 1:14:60 of L-asparaginase-albumin:insulin was used. The separated conjugate had a molecular weight of $1.2 \times 10^6$ Daltons.

The physiological properties of this conjugate were very similar to those of the conjugates produced in accordance with Example 1.

EXAMPLE 3

α-1,4-Glucosidase-Albumin-Insulin Conjugate Cross-Linked with Glutaraldehyde or Carbodiimide Human placental α-1,4-glucosidase (2 mg, 150 units) was cross-linked with human albumin (20 mg) using 5 μg of glutaraldehyde. The reaction conditions of Example 1 were maintained except that the enzyme substrate included was p-nitrophenyl glucoside. The resulting enzyme-albumin complex was then cross-linked to insulin (2 mg) using either glutaraldehyde or ECDI, again in accordance with the conditions of Example 1. The separated end product had a molecular weight of $1 \times 10^6$ Daltons when a molar ratio of 1:12:12 of enzyme:albumin:insulin was used. Some properties of these conjugates are shown in Tables II, IV and V.

The end product was tested for enzyme activity in accordance with the procedure of de Barsy et al., Eur. J. Biochem., 31, 1972, pg. 156–165. As indicated in Table II, the conjugate retained enzyme activity against an artificial substrate p-nitrophenyl glucose, against maltose and against its natural substrate human glycogen (from liver).

The binding specificity of the enzyme conjugate was tested by covalently labelling the conjugate with $^{125}$Iodine and then incubating the conjugate with mouse spleen cells or chick embryonic muscle cells in accordance with the procedure indicated in Example 1. The data in Table IV illustrates the binding of the enzyme-albumin-insulin conjugate to cells known to be high in insulin receptor activity. By subcelluler fractionation of the tissue, it was found that the conjugate had been internalized by the cell and was associated with a lysosomal fraction. The enzyme can be located within the cell in a fraction rich in acid phosphatase activity known to be contained within lysosomes. Thus the insulin targeting agent was shown not to interfere with the ability of the body cell to utilize the α-1,4-glucosidase therapeutic agent.

TABLE IV

PREFERENTIAL BINDING OF INSULIN-CONJUGATED ENZYME-ALBUMIN CONJUGATES TO SPLEEN CELLS AND TO MUSCLE CELLS

| Enzyme Preparation | Spleen Cells % Uptake | Muscle Cells* |
|---|---|---|
| L-Asparaginase | 0.81 | |
| L-Asparaginase-Albumin | 2.78 | |
| L-Asparaginase-Albumin-Insulin | 22.70 | |
| α-1,4-Glucosidase | 6.5 | 8.7 |
| α-1,4-Glucosidase-Albumin | 6.9 | 9.0 |
| α-1,4-Glucosidase-Albumin-Insulin | 28.1 | 30.1 |

*Enzyme preparations were labelled covalently with $^{125}$Iodine and then co-incubated with either mouse spleen cells or chick embryonic muscle cells and the % binding of the enzyme determined after 20 min. at 24° C.

TABLE V

IMMUNOGENICITY OF ENZYME AND ENZYME-ALBUMIN* CONJUGATES

| Enzyme Preparation | Immunogenicity** |
|---|---|
| L-Asparaginase*** | +++ |
| L-Asparaginase-Albumin (1:5) | + |
| L-Asparaginase-Albumin (1:10) | − |
| L-Asparaginase-Albumin (1:20) | − |

TABLE V-continued
IMMUNOGENICITY OF ENZYME AND ENZYME-ALBUMIN* CONJUGATES

| Enzyme Preparation | Immunogenicity** |
|---|---|
| α-1,4-Glucosidase**** | +++ |
| α-1,4-Glucosidase-Albumin (1:10) | — |
| α-1,4-Glucosidase-Albumin-Insulin (1:10:60) | — |

*Homologous albumin is used in all cases: rabbit albumin if immunogenicity testing is to be performed in rabbits and mouse albumin if testing is performed in mice. Testing is as described (Remy & Poznansky, The Lancet, ii, (1978), 68–70).
**Immunogenicity scored on radioimmunoassay as - no reaction, + slight reaction to +++ strong reaction.
***L-asparaginase is from E. coli.
****α-1,4-Glucosidase is from human placenta

EXAMPLE 4
L-Asparaginase-Albumin-IgG Conjugate Cross-Linked with Glutaraldehyde and Sodium Periodate L-asparaginase-albumin conjugates were prepared using glutaraldehyde as a cross-linking agent and the conditions set forth in Example 1 (2.5 mg L-asparaginase, 20 mg albumin, 5 μg glutaraldehyde and 5 mg L-asparagine). The resulting conjugate was then cross-linked to a monoclonal antibody (5.0 mg of anti-H-2$^k$, an antibody against the mouse histocompatibility antigen H-2$^k$, prepared according to Kennett, R. H. et al. (1980) "Monoclonal Antibody Hybridomas: A New Dimension in Biological Analyses. Plenum Press, New York) using 5 mg of sodium periodate for 2 hours at 4° C. The cross-linking procedure utilizes a sugar residue on the Fc fragment of the antibody and the amino groups on the enzyme-albumin conjugate. The resultant conjugate was separated as described in Example 1 and was found to have a molecular weight of 1.1×10$^6$ Daltons and a calculated mole ratio of 1:10:2, L-asparaginase:albumin:anti-H-2$^k$ antibody.

Using methods similar to those described in Example 1, the resulting conjugate was found to retain enzyme activity (see Table II) toward the substrate L-asparagine. Two types of experiments indicate that the conjugate binds preferentially to cells which possess the corresponding H-2$^k$ antigen but not to cells which possess a different histocompatibility antigen, the H-2$^d$ antigen. When 1 μg of conjugate (labelled with $^{125}$I) is incubated with 5×10$^6$ Balb/Ccr spleen cells which contain the H-2$^d$ antigen less than 2% of the conjugate binds to the cells. When the same amount of conjugate is incubated with the same number of spleen cells from C3H mice which contain the H-2$^k$ antigen 45% of the conjugate was found bound to the cells after a 2 hour incubation at 18° C. This experiment is an in-vitro experiment where the cells were grown in a tissue culture flask. Table VI demonstrates that the preferential binding of the targeted conjugates persists in whole animal experiments. A significant increase in the retention of $^{125}$I-labelled conjugate is observed when the conjugate (containing the anti-H-2$^k$ antibody) is injected into Balb/Ccr mice (which possess the H-2$^d$ antigen) which have been inoculated with tumor cells (RC3HED cells which possess the H-2$^k$ antigen). This suggests strongly that the conjugate is binding preferentially to the tumor cells in the whole animal experiment. The use of the histocompatibility antigen (H-2$^d$ and H-2$^k$ in mice) presents a convenient cell surface antigen commonly found in varying mouse strains. The analagous use of human histocompatibility antigens as cell surface targets (i.e. using the corresponding antibody) might be expected to be useful if this provides a proper target for a given enzyme or drug therapy.

TABLE VI
IN-VIVO TARGETING OF L-ASPARAGINASE CONJUGATES TO TUMOR CELLS

| | % $^{125}$I-Labelled Enzyme Remaining | | |
|---|---|---|---|
| | 15 h | 24 h | 48 h |
| Free L-Asparaginase | 9% | 4% | 3% |
| L-Asparaginase-Albumin | 41% | 17% | 11% |
| L-Asparaginase-Albumin-Anti-H-2$^k$ Antibody | 74% | 51% | 37% |

Balb/Ccr mice possessing the H-2$^d$ antigen were injected with C63HED tumor cells which possess the H-2$^k$ antigen. $^{125}$I-labelled enzyme preparations were injected intravenously into the mice and the % label remaining determined after varying time periods.

EXAMPLE 5
L-Asparaginase-Albumin-(Fab')$_2$ Fragment of IgG Conjugates

L-Asparaginase-albumin conjugates were prepared using the glutaraldehyde cross-linking agent and the conditions set forth in Example 4. The resulting conjugate was then cross-linked to an equal molar quantity of the (Fab')$_2$ fragment of the monoclonal anti-H-2$^k$ antibody using either sodium periodate or ECDI as the cross-linking agent. The resulting end conjugate had a molecular weight of about 1×10$^6$ Daltons. The procedure was exactly as in Example 4 except that only the (Fab')$_2$ fragment of the antibody molecule was used.

In testing procedures similar to those of Examples 1 and 4, the enzyme-albumin-(Fab')$_2$ conjugate was found to retain both L-asparaginase activity (see Table II) and binding affinity to cells possessing the H-2$^k$ antigen. The binding specificity was shown to exist in both tissue culture and whole animal (mouse) experiments as described in Example 4.

The IgG targeting agent used in Example 4 included both the Fc fragments and the (Fab')$_2$ fragments. The use of the (Fab')$_2$ fragments only in the present example is preferred since conjugates of the (Fab')$_2$ fragments retain the ligand properties of the antibody for binding specifically to antigen receptors, while the possibility of the conjugate binding to the less specific Fc receptors is removed. Fc receptors are found on a wider range of cell types. Further, use of the (Fab')$_2$ fragment in place of the entire IgG molecule has the added advantage of rendering the entire polymeric complex less immunogenic because of the absence of the Fc fragment.

EXAMPLE 6
α-1,4-Glucosidase-Albumin-Immunoglobulin Conjugates

Conjugates of α-1,4-glucosidase and albumin were produced in accordance with the conditions of Example 3. The conjugates were then chemically linked to a heterologous rabbit immunoglobulin preparation that had been prepared against isolated rat hepatocytes. The mole ratio was 1:10:2, α-1,4-glucosidase:albumin:immunoglobulin. Both the ECDI or glutaraldehyde cross-linking conditions were found to be successful in this linking step. The separated enzyme-albumin-immunoglobulin conjugate had a molecular weight of 1.2×10$^6$ Daltons and was composed of an average of one molecule enzyme, twelve molecules albumin and one and a half molecules of antibody.

Testing procedures similar to those used in the previous examples showed that the final conjugate retained enzymatic activity (see Table II). The complex also was shown to be taken up preferentially by rat hepatocytes over other cell types in whole animal experiments (see Table VII). Comparison of the data in Table VII for the α-1,4-glucosidase-albumin-immunoglobulin (control) conjugate and the α-1,4-glucosidase-albumin-immunoglobulin (anti-hepatocyte) conjugate shows that preferential uptake by hepatocytes occurs only when the immunoglobulin molecule is directed against hepatocytes.

The prepared enzyme-albumin-immunoglobulin conjugates were found to give similar results whether the intact immunoglobulin molecules or only the (Fab')$_2$ fragments were used as the targeting agent.

TABLE VII
TARGETING OF ENZYME-ALBUMIN-IMMUNOGLOBULIN CONJUGATES TO RAT HEPATOCYTES

| Enzyme Preparation | Hepatocyte/Kupffer Cells |
|---|---|
| α-1,4-Glucosidase | 0.10 |
| α-1,4-Glucosidase-Albumin | 0.17 |
| α-1,4-Glucosidase-Albumin-Immunoglobulin (Control)* | 0.16 |
| Immunoglobulin (Anti-Hepatocyte) | 0.91 |
| α-1,4-Glucosidase-Albumin-Immunoglobulin (Anti-Hepatocyte) | 1.23 |

*Control immunoglobulin was one which was not directed against rat hepatocytes.

$^{125}$I-labelled enzyme and enzyme conjugate preparations were injected into rats at time zero. After 90% of the label had cleared from the circulation, the liver was excised. The Kupffer cells and hepatocytes were then separated and the percent label in each fraction was determined.

EXAMPLE 7
L-Asparaginase-Albumin-Human Pancreatic Tumor Cell Antibody Conjugates L-Asparaginase was cross-linked with human serum albumin and antibody in accordance with the procedure set forth in Example 4 with the exception that the antibody was a monoclonal antibody directed against human pancreatic tumor cells. Human pancreatic tumor cells were grown in suspension culture in accordance with the techniques described by Yunis, A. A. et al., Int. J. Cancer, 19, (1977), pg. 128. Monoclonal antibodies against the cells were produced as described in the Kennett reference cited in Example 4.

In accordance with the previous test procedures, the enzyme conjugate was shown to retain enzyme activity and to be non-immunogenic and resistant to bioinactivation. These tests results were similar to those obtained for the L-asparaginase conjugates of Example 4. The enzyme-albumin-antibody conjugates were found to be significantly more cytotoxic to human pancreatic tumor cells grown in tissue culture than L-asparaginase alone, L-asparaginase linked to albumin, L-asparaginase linked to albumin and a non-specific antibody or non-specific monoclonal antibody, or the monoclonal antibody against pancreatic tumor cell itself (see Table VIII).

This is an important finding since there is no known effective treatment for cancer of the pancreas and yet Yunis and co-workers in Int. J. Can., 19, (1977), pg. 128-135, have demonstrated that human pancreatic tumor cells in tissue culture are asparaginase sensitive.

TABLE VIII
CYTOTOXICITY OF L-ASPARAGINASE-CONJUGATES TO HUMAN PANCREATIC TUMOR CELLS GROWN IN TISSUE CULTURE

| Enzyme Preparation | Dose Required to Inhibit Growth for Three Days |
|---|---|
| L-asparaginase | 0.08 Units* |
| L-asparaginase-albumin | 0.02 Units* |
| L-asparaginase-albumin-antibody (control) | 0.03 Units* |
| L-asparaginase-albumin-antibody (expt.) (expt. = monoclonal antibody against pancreatic (human) tumor cells) | 0.005 Units* |

*Units are defined in the Mashburn paper cited in Example 1.

A number ($5 \times 10^5$) of human pancreatic tumor cells were seeded in a tissue culture flask at time zero and the dose required to completely inhibit tumor cell growth over a period of 3 days for the different enzyme preparations was determined. The monoclonal antibody alone was ineffective at inhibiting tumor cell growth at the concentration used in the conjugate.

EXAMPLE 8
Superoxide Dismutase-Albumin-Hyaluronic Acid Antibody Conjugates

In a manner analogous to Example 1, glutaraldehyde was used to link the enzyme superoxide dismutase (from hog liver) to albumin to antibodies against hyaluronic acid (rabbit antisera). Using a molar ratio of 1:10:1 of enzyme to albumin to antibody a conjugate having a molecular weight of $1.1 \times 10^6$ was formed.

In test procedures analogous to those of Example 1, the conjugate was found to resist bioinactivation and to be non-immunogenic. In addition, the conjugate showed a high affinity for the substrate hyaluronic acid.

The benefit of cross-linking superoxide dismutase to albumin has been shown previously, see Wong, Cleland and Poznansky, Agents and Actions, (1980), 10, pg. 231-244. The present conjugates with the antibody against hyaluronic acid can be targeted against sites containing hyaluronic acid to reduce inflammation associated with rheumatoid arthritis.

While the present invention has been disclosed in connection with the preferred embodiment thereof, it should be understood that there may be other embodiments which fall within the spirit and scope of the invention as defined by the following claims.

The embodiments of the invention in which an exclusive property or privilege is claimed are defined as follows:

1. A water soluble, sterile and non-immunogenic composition of matter, comprising an enzyme selected from the group consisting of α-1,4-glucosidase, L-asparaginase, and superoxide dismutase, said enzyme chemically linked to homologous albumin, and a targeting agent chemically linked to the albumin, the amount of albumin being sufficient to mask antigenicity of the enzyme, and the targeting agent having binding specificity for receptor sites on cells to which it is desirable to direct the enzyme.

2. The composition as set forth in claim 1, wherein the targeting agent is selected from the group consisting of serum hormones and cell specific antibodies.

3. The composition as set forth in claim 1, wherein the targeting agent is insulin.

4. The composition as set forth in claim 1, wherein the targeting agent is an antibody directed against human pancreatic tumor cells.

5. The composition as set forth in claim 1, wherein the targeting agent is an immunoglobulin.

6. The composition as set forth in claim 1, wherein the targeting agent is the (Fab')$_2$ fragment of an immunoglobulin G molecule.

7. The composition as set forth in claim 3, wherein the enzyme is selected from the group consisting of α-1,4-glucosidase and L-asparaginase.

8. The composition as set forth in claim 4, wherein the enzyme is L-asparaginase.

9. The composition as set forth in claim 5, wherein the enzyme is selected from the group consisting of α-1,4-glucosidase and L-asparaginase.

10. The composition as set forth in claim 6, wherein the enzyme is selected from the group consisting of α-1,4-glucosidase and L-asparaginase.

11. The composition as set forth in claim 1, wherein the targeting agent is an antibody against hyaluronic acid, and the enzyme is superoxide dismutase.

* * * * *